(12) United States Patent
Dotan et al.

(10) Patent No.: US 6,569,199 B1
(45) Date of Patent: May 27, 2003

(54) TELESCOPIC INTRAOCULAR LENS

(76) Inventors: Gideon Dotan, 32 Havradim Street, Yehud 56275 (IL); Eli Aharoni, 20/136 Habad Street, Rishon le Zion 75302 (IL); Isaac Lipshitz, 89A Hanasi Street, Herzliya Pituach 36448 (IL); David Klein, 4 Shaar Hagai Street, Rehovot 76509 (IL)

(*) Notice: Subject to any disclaimer, the term of this patent is extended or adjusted under 35 U.S.C. 154(b) by 0 days.

(21) Appl. No.: 09/678,559

(22) Filed: Oct. 3, 2000

Related U.S. Application Data

(63) Continuation of application No. 09/222,330, filed on Dec. 29, 1998, now abandoned.

(51) Int. Cl.⁷ ................................................. A61F 2/16
(52) U.S. Cl. ................................... 623/6.17; 623/6.11
(58) Field of Search .......................... 623/6, 6.17, 6.11

(56) References Cited

U.S. PATENT DOCUMENTS

| | | |
|---|---|---|
| 4,373,218 A | 2/1983 | Schachar |
| 4,676,791 A | 6/1987 | LeMaster et al. |
| 4,678,469 A | 7/1987 | Kelman |
| 4,759,761 A | 7/1988 | Portnoy |
| 4,955,904 A | 9/1990 | Atebara et al. |
| 4,968,127 A | 11/1990 | Russell et al. |
| 4,976,732 A | 12/1990 | Vorosmarthy |
| 5,203,789 A | 4/1993 | McDonald |
| 5,343,335 A | 8/1994 | Hara |
| 5,354,335 A | 10/1994 | Lipshitz et al. |
| 5,391,202 A | 2/1995 | Lipshitz et al. |
| 5,425,759 A | 6/1995 | McDonald |
| 5,549,670 A | 8/1996 | Young et al. |
| 5,769,889 A * | 6/1998 | Kelman .......................... 623/6 |
| 5,814,103 A | 9/1998 | Lipshitz et al. |

FOREIGN PATENT DOCUMENTS

| | | |
|---|---|---|
| EP | 0 419 740 | 9/1989 |
| GB | 2 181 355 | 4/1987 |

\* cited by examiner

*Primary Examiner*—Corrine McDermott
*Assistant Examiner*—Hieu Phan

(57) ABSTRACT

An intraocular lens implant including a telescope body defining an optical path for light to pass therethrough, at least one lens attached to the telescope body, mounting structure connected to the telescope body for mounting the implant in an eye, and an optical blocker disposed in the implant outside of the optical path which minimizes a transmission of light outside the optical path but does not impede transmission of light through the optical path.

2 Claims, 1 Drawing Sheet

TELESCOPIC INTRAOCULAR LENS

REFERENCE TO RELATED APPLICATIONS

This is a continuation application of U.S. patent application Ser. No. 09/222,330, filed Dec. 29, 1998 now abandoned.

FIELD OF THE INVENTION

The present invention relates generally to intraocular lens (IOL) implants and particularly to a telescopic intraocular lens with anti-glare structure.

BACKGROUND OF THE INVENTION

Intraocular lens (IOL) inserts comprising telescopes are known. Representative examples of telescopic IOL's include applicant/assignee's U.S. Pat. Nos. 5,354,335; 5,391,202 and 5,814,103, the disclosures of which are incorporated herein by reference. Telescopic IOL's may be classified as Galilean or reverse Galilean. Galilean telescopic IOL's are designed to correct problems stemming from central field defects, such as those caused by macular degeneration (e.g., atrophic or exudative), chorioretinitis of the macula, central serous chorioretinopathy, or ischemia, for example. Reverse Galilean telescopic IOL's are designed to correct problems stemming from peripheral field defects, such as those caused by retinitis pigmentosa, primary or metastatic central nervous system tumors or glaucoma, for example.

A telescopic IOL is designed to correct visual problems by channeling incoming light rays through the telescope to the retina. Generally the telescope is placed to direct the light rays to the area of the macula lutea, commonly referred to as the yellow spot. The center of the yellow spot, called the fovea centralis, is the point of acutest vision; hence, the preference of directing the light thereat. A problem which can occur with telescopic IOL's is that light enters the wearer's eye not only through the telescope but through other portions of the IOL, such as carrier structure. The stray light which does not pass through the telescope is not focused towards the retina in the same manner as the light which does pass through the telescope. The stray light causes glare to the wearer of the IOL and reduces contrast between perceived figures.

SUMMARY OF THE INVENTION

The present invention seeks to provide an improved telescopic IOL with anti-glare structure. Specifically, the present invention provides an optical blocker which minimizes a transmission of light outside an optical path defined by a telescope body of the implant, but does not impede transmission of light through that optical path. The optical blocker may be translucent or opaque. Translucent is defined as a medium which transmits ray of light so diffused that objects cannot be seen distinctly. The present invention thus solves the abovementioned problem of the prior art problem by reducing or eliminating stray light outside of the optical path of the telescope, thereby reducing or eliminating glare to the wearer of the IOL and maintaining contrast between perceived figures.

There is thus provided in accordance with a preferred embodiment of the present invention an intraocular lens implant including a telescope body defining an optical path for light to pass therethrough, at least one lens attached to the telescope body, mounting structure connected to the telescope body for mounting the implant in an eye, and an optical blocker disposed in the implant outside of the optical path which minimizes a transmission of light outside the optical path but does not impede transmission of light through the optical path.

BRIEF DESCRIPTION OF THE DRAWINGS

The present invention will be understood and appreciated more fully from the following detailed description, taken in conjunction with the drawings in which.

DETAILED DESCRIPTION OF A PREFERRED EMBODIMENT

Figure 1:
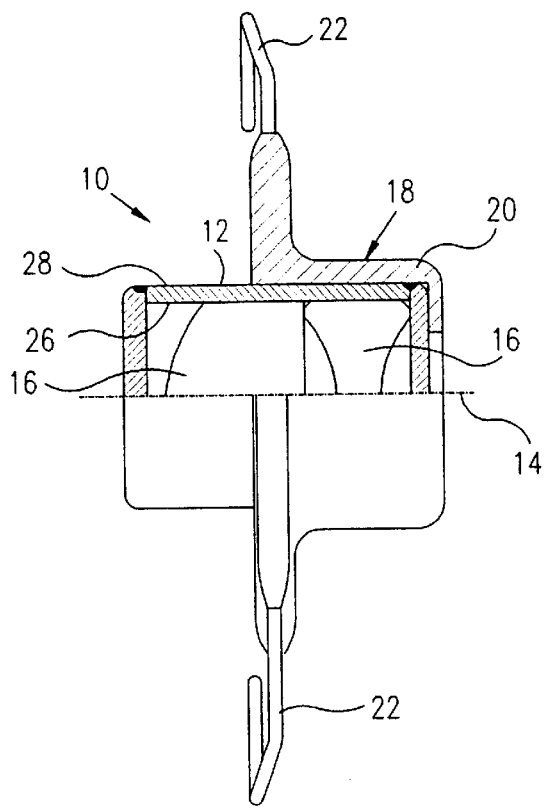
FIG. 1 is a simplified partially sectional illustration of an intraocular lens implant constructed and operative in accordance with a preferred embodiment of the present invention.

Reference is now made to FIG. 1 which illustrates an intraocular lens (IOL) implant 10 constructed and operative in accordance with a preferred embodiment of the present invention. IOL implant 10 preferably includes a telescope body 12 defining an optical path 14 for light to pass therethrough. Telescope body 12 is preferably generally cylindrical and may be constructed in accordance with the teachings of applicant/assignee's U.S. Pat. Nos. 5,354,335; 5,391,202 and 5,814,103. As described in these references, telescope body 12 includes one or more lenses 16, preferably at least two, forming either a Galilean (having an anteriorly positioned positive lens and a posteriorly positioned negative lens) or reverse Galilean (having an anteriorly positioned negative lens and a posteriorly positioned positive lens) telescope.

Mounting structure 18 is provided for mounting IOL implant 10 in an eye (not shown). Mounting structure 18 may include, for example, a carrier element 20 secured to an outside periphery of telescope body 12 from which extend one or more haptics 22.

A suitable material for constructing all parts of IOL implant 10, as is well known in the art, is polymethylmethacrylate (PMMA), for example.

It is a particular feature of the present invention that an optical blocker is disposed in IOL implant 10 outside of optical path 14 which minimizes a transmission of light outside optical path 14 but does not impede transmission of light through optical path 14. Several examples of such an optical blocker are now described.

In accordance with one preferred embodiment of the present invention, the optical blocker comprises a translucent or opaque coloring in a portion of telescope body 12 outside of optical path 14. For example, a translucent or opaque coating may be painted or otherwise formed on an inner perimeter 26 or outside perimeter 28 of telescope body 12. Additionally or alternatively, the material of telescope body 12 may be made translucent or opaque. Colored PMMA is known and available and is used, for example, in portions of some non-telescope IOL's of Morcher GmbH of Stuttgart, Germany.

Most preferably the optical blocker comprises a similarly described translucent or opaque coloring in mounting structure 18 outside of optical path 14, such as a translucent or opaque coating formed on carrier element 20 or by manufacturing carrier element 20 from colored PMMA.

Figure 2:
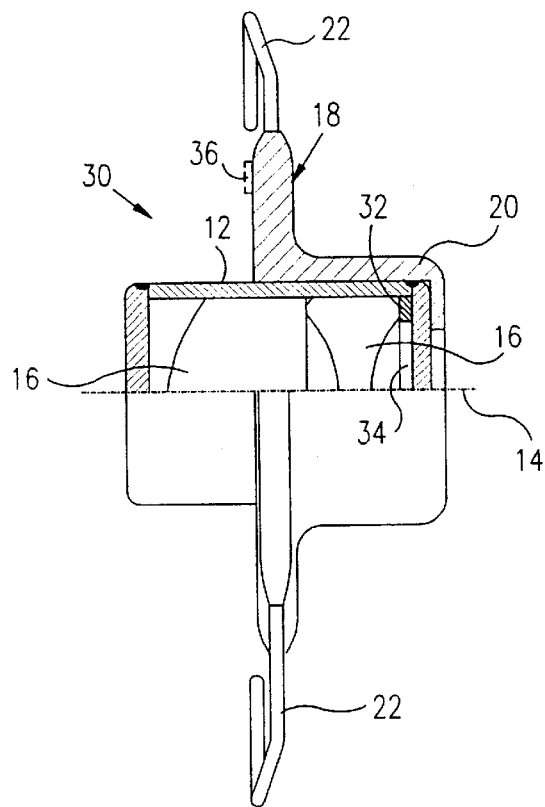
FIG. 2 is a simplified partially sectional illustration of an intraocular lens implant constructed and operative in accordance with another preferred embodiment of the present invention.

Reference is now made to FIG. 2 which illustrates an intraocular lens (IOL) implant 30 constructed and operative in accordance with another preferred embodiment of the present invention. IOL implant 30 is preferably similar to IOL implant 10 with like elements being designated by like numerals. IOL implant 30 differs from IOL implant 10 in that in implant 30 the optical blocker comprises a translucent or opaque annulus 32 disposed in telescope body 12. Annulus 32 has an aperture 34 aligned with optical path 14 such that transmission of light through optical path 14 is not impeded by annulus 32.

Another alternative for constructing the translucent or opaque optical blocker of the present invention is by using electrochromic materials. Electrochromic materials have the property of changing from opaque or translucent to transparent in the presence of an electric field. Some examples are liquid crystals of indium-tin oxide (ITO) or electrochromic glasses based on tungsten oxide. A suitable miniature power source (reference numeral 36 in FIG. 2) would be electrically connected to the electrochromic material to produce the required electrical field. In such an embodiment, the optical blocker would thus selectively block light, i.e., the optical blocker would either allow light to pass through outside the optical path of the telescope body or block the light, as desired.

It will be appreciated by persons skilled in the art that the present invention is not limited by what has been particularly shown and described hereinabove, Rather the scope of the present invention includes both combinations and sub-combinations of the features described hereinabove as well as modifications and variations thereof which would occur to a person of skill in the art upon reading the foregoing description and which are not in the prior art.

What is claimed is:

1. An intraocular lens implant comprising:

a telescope housing defining an optical path for light to pass therethrough;

a plurality of lenses attached to said telescope body;

mounting structure connected to said telescope body for mounting said implant in an eye; and an optical blocker disposed inside of and separate from said housing and outside of and separate from said lenses in said implant outside of said optical path which minimizes a transmission of light outside said optical path but does not impede transmission of light through said optical path, wherein said optical blocker comprises a translucent annulus disposed in said telescope body, said annulus having an aperture aligned with said optical path such that transmission of light through said optical path is not impeded by said annulus.

2. An intraocular lens implant comprising:

a telescope housing defining an optical path for light to pass therethrough;

a plurality of lenses attached to said telescope body;

mounting structure connected to said telescope body for mounting said implant in an eye; and an optical blocker disposed inside of and separate from said housing and outside of and separate from said lenses in said implant outside of said optical path which minimizes a transmission of light outside said optical path but does not impede transmission of light through said optical path, wherein said optical blocker comprises an opaque annulus disposed in said telescope body, said annulus having an aperture aligned with said optical path such that transmission of light through said optical path is not impeded by said annulus.

* * * * *

UNITED STATES PATENT AND TRADEMARK OFFICE
CERTIFICATE OF CORRECTION

PATENT NO.    : 6,569,199 B1
DATED         : May 27, 2003
INVENTOR(S)   : Gideon Dotan et al.

It is certified that error appears in the above-identified patent and that said Letters Patent is hereby corrected as shown below:

<u>Title page,</u>
Insert item -- [73] Assignee: Visioncare Ophthalmic Technologies, Inc.
                              Saratoga, California --

Signed and Sealed this

Ninth Day of March, 2004

JON W. DUDAS
*Acting Director of the United States Patent and Trademark Office*